United States Patent
Wang et al.

(10) Patent No.: US 9,459,358 B2
(45) Date of Patent: Oct. 4, 2016

(54) REFERENCE CALIBRATION IN PHOTON COUNTING BASED SPECTRAL CT

(71) Applicant: TOSHIBA MEDICAL SYSTEMS CORPORATION, Tochigi (JP)

(72) Inventors: Xiaolan Wang, Buffalo Grove, IL (US); Yu Zou, Naperville, IL (US); Adam Petschke, Lake Bluff, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 147 days.

(21) Appl. No.: 14/103,137

(22) Filed: Dec. 11, 2013

(65) Prior Publication Data

US 2015/0160355 A1    Jun. 11, 2015

(51) Int. Cl.
G01T 7/00    (2006.01)
G01N 23/04   (2006.01)
A61B 6/00    (2006.01)

(52) U.S. Cl.
CPC .............. G01T 7/005 (2013.01); A61B 6/585 (2013.01); G01N 23/046 (2013.01)

(58) Field of Classification Search
CPC ........ A61B 6/58; A61B 6/582; A61B 6/585; G01T 1/36; G01T 7/005
See application file for complete search history.

(56) References Cited

U.S. PATENT DOCUMENTS

| 7,693,252 B2* | 4/2010 | Noshi | A61B 6/00 378/4 |
| 8,917,811 B2* | 12/2014 | Zhang | G01N 23/046 378/16 |
| 9,020,092 B2* | 4/2015 | Wang | A61B 6/583 378/5 |
| 9,155,516 B2* | 10/2015 | Wang | A61B 6/4241 |
| 2006/0274877 A1* | 12/2006 | Noshi | A61B 6/00 378/4 |
| 2012/0087463 A1* | 4/2012 | Greenberg | G01T 7/005 378/5 |
| 2013/0308848 A1* | 11/2013 | Proksa | A61B 6/032 382/131 |
| 2014/0105370 A1* | 4/2014 | Yamakawa | A61B 6/025 378/207 |
| 2014/0226788 A1* | 8/2014 | Radley | G01N 23/087 378/64 |
| 2014/0233693 A1* | 8/2014 | Wang | A61B 6/4241 378/5 |
| 2014/0233694 A1* | 8/2014 | Wang | A61B 6/583 378/5 |
| 2014/0328451 A1* | 11/2014 | Zhang | G01T 7/005 378/5 |
| 2015/0160355 A1* | 6/2015 | Wang | G01N 23/046 378/19 |
| 2016/0095564 A1* | 4/2016 | Kato | A61B 6/52 378/19 |

* cited by examiner

*Primary Examiner* — Thomas R Artman
(74) *Attorney, Agent, or Firm* — Oblon, McClelland, Maier & Neustadt, L.L.P.

(57) ABSTRACT

Calibrating a photon-counting detector can include receiving a reference signal, by circuitry, where the reference signal is measured by a reference detector that measures an output from an X-ray tube. Determining circuitry can then determine, for a detector channel of the photon-counting detector, a mapping between a first true count rate on the detector channel without an object and the reference signal in accordance with a linear relationship between the reference signal and the first true count rate, based on a measured count rate on the detector channel and a predefined relationship between the first true count rate and the measured count rate.

20 Claims, 8 Drawing Sheets

REFERENCE CALIBRATION IN PHOTON COUNTING BASED SPECTRAL CT

FIELD

This disclosure relates to reference calibration for an imaging system, especially in a spectral computed tomography (CT) system.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed. In the reconstruction, the map of the linear attenuation coefficient (LAC) of the imaged subjects is obtained from the line integrals of the LAC through an inverse Radon transform. The line integrals can be related to the logarithm of the primary intensity of the X-rays passing through the subject. However, the measured X-ray intensity on the detector may include both scattering photons and primary photons. Thus, in images reconstructed from scattering, contaminated intensities may contain some scattering artifacts.

A third-generation ($3^{rd}$-generation) CT system can include sparsely distributed photon-counting detectors (PCDs). In such a combined system, the PCDs collect primary beams through a range of detector fan angles.

Clinical applications can benefit from spectral CT technology, which can provide an improvement in material differentiation and beam hardening correction. Further, semiconductor-based photon-counting detectors are a promising candidate for spectral CT and are capable of providing better spectral information compared to conventional spectral CT technology (e.g., dual-source, kVp-switching, etc.).

Due to dead time (~100 ns), which is determined by the type of semiconductor (e.g. CZT or CdTe), its thickness, and readout circuit, pulse pile-up or pileup at high X-ray flux (~$10^8$ cps/mm$^2$) can be very severe, and measured spectral signals can be distorted. The distorted spectral signals can cause artifacts in the reconstructed images. Furthermore, the dead time is not a constant for a given readout circuit due to the location of the pulse formation within the detector cell. However, if the pile-up effect can be corrected in the detector model, then the image quality can be improved.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION

According to one implementation, an apparatus for calibrating a photon-counting detector can include circuitry configured to: receive a reference signal, which is measured by a reference detector that measures an output from an X-ray tube, and determine, for a detector channel of the photon-counting detector, a mapping between a first true count rate on the detector channel without an object and the reference signal in accordance with a linear relationship between the reference signal and the first true count rate, based on a measured count rate on the detector channel and a predefined relationship between the first true count rate and the measured count rate.

The circuitry can be further configured to: determine the mapping for each of a plurality of detector channels of a plurality of photon-counting detectors, and for each of a plurality of combinations of bowtie and peak kilovoltage of the X-ray tube, and store a plurality of corresponding values for the mapping.

The circuitry can be further configured to: calculate second true count rates on the detector channel based on the stored values for the mapping and reference signals from the reference detector during a scan of the object; calculate third true count rates on the detector channel with the object based on the calculated second true counts and a basis material thickness of the object; and apply the third true count rates to raw data pile-up correction and calculate projection data based thereon for each of the detector channels and for each of a plurality views of the object. The circuitry can be further configured to generate images from the projection data.

The circuitry can be further configured to determine the mapping for each of a plurality of polar angles. The circuitry can be further configured to: calculate second true count rates on the detector channel based on the stored values for the mapping and reference signals from the reference detector during a scan of the object; calculate third true count rates on the detector channel with the object based on the calculated second true counts and a basis material thickness of the object; and apply the third true count rates to raw data pile-up correction and calculate projection data based thereon for each of the plurality of polar angles and for each of the detector channels. The circuitry can be further configured to generate images from the projection data.

The predefined relationship between the first true count rate, $n_{PCD}^{air}$, and the measured count rate can be $\hat{n}_{PCD}^{air}=f(n_{PCD}^{air})=f(A \cdot I_{ref})$ where $\hat{n}_{PCD}^{air}$ is the measured count rate, f is a reference calibration function that reflects a pile-up effect resulting in count loss and non-linearity, $I_{ref}$ is the reference signal, and A is the mapping and is a derived parameter that does not depend on properties of the photon-counting detector. $f(A \cdot I_{ref})$ can be equal to one of:

$$A \cdot I_{ref} e^{-\tau A I_{ref}}, \quad \frac{A \cdot I_{ref}}{1+\tau A I_{ref}}, \text{ and } \frac{1}{\tau}(1-e^{-\tau A I_{ref}});$$

and τ can be a calibration parameter that describes a linearity of a measured count rate of the photon-counting detector.

The predefined relationship between the first true count rate, $n_{PCD}^{air}$ and the measured count rate can be:

$n_{PCD}{}^{air} = A \cdot I_{ref}$, and $n'_{PCD}{}^{air} = A' \cdot I_{ref} = n_{PCD}{}^{air} \int dE S^{air}(E) e^{-\mu_F(E) l_F}$, where $I_{ref}$ is the reference signal, $\mu_F(E)$ is a linear attenuation coefficient of an additional filter that is provided between the X-ray tube and the photon counting detector, $n'_{PCD}{}^{air}$ is the measured count rate with the additional filter, $l_F$ is a path length in the additional filter, $S^{air}$ indicates a spectrum in air, A is the mapping, A' is the mapping with the additional filter, and $A' = A \int dES^{air}(E) e^{-\mu_F(E) l_F}$. The predefined relationship between the first true count rate, $n_{PCD}{}^{air}$, and the measured count rate can be: $n_{PCD}{}^{air}$, and $N(E) = T_{PCD}\{ne^{-n\tau}\int dE_0 R_1(E,E_0)S(E_0) + n^2 e^{-n\tau}\int\int dE_0 dE_1 R_2(E,E_0,E_1)S(E_0)S(E_1)\}$, where $n = n_{PCD}{}^{air}$, N(E) is a measured number of counts from the photo counting detector in an energy bin E that has a particular energy range, S is a spectrum, $R_1$ and $R_2$ are detector response functions, $I_{ref}$ is the reference signal, A is the mapping, n is solved for various currents to determine a relationship to $I_{ref}$, and after n is obtained, the relationship between n and $I_{ref}$ is utilized to find A, according to $n_{PCD}{}^{air} = A \cdot I_{ref}$.

The predefined relationship between the first true count rate, $n_{PCD}{}^{air}$, and the measured count can be: $n_{PCD}{}^{air} = A \cdot I_{ref}$, and $n' = n_{PCD}{}^{air} \int dE_0 S(E_0) e^{-\mu_1(E_0)L_1 - \mu_2(E_0)L_2}$, where n' is the measured count rate, $L_1$ and $L_2$ represent a basis thickness of a phantom provided between the X-ray tube and the photon counting detector and $\mu_1$ and $\mu_2$ are corresponding linear attenuation coefficients of the phantom, $I_{ref}$ is the reference signal, A is the mapping, and $E_0$, is a true energy of an incident X-ray from the X-ray tube and two or more values for the true energy are utilized.

The apparatus can include: the X-ray tube; a bowtie filter provided between the X-ray tube and a scanning area for scanning an object; the reference detector provided such that a portion of the X-rays output from the X-ray tube are detected by the reference detector; and photon detectors to measure X-ray intensity and a spectrum of X-rays from the X-ray tube that pass through the scanning area. The reference detector can be provided on or proximate to the bowtie filter on a side of the bowtie filter that is opposite to the X-ray tube such that a portion of the X-rays output from the X-ray tube pass through the bowtie filter and are detected by the reference detector. The reference detector can be provided on or proximate to the bowtie filter, between the bowtie filter and the X-ray tube, such that a portion of the X-rays output from the X-ray tube are detected by the reference detector without passing through the bowtie filter.

The reference detector can be an energy-integrating detector, only measures X-ray intensity variations, and does not measure spectrum variation.

In one implementation, a method for calibrating a photon-counting detector can include receiving, by receiving circuitry, a reference signal, which is measured by a reference detector that measures an output from an X-ray tube, and determining, by determining circuitry, for a detector channel of the photon-counting detector, a mapping between a first true count rate on the detector channel without an object and the reference signal in accordance with a linear relationship between the reference signal and the first true count rate, based on a measured count rate on the detector channel and a predefined relationship between the first true count rate and the measured count rate.

In one implementation, a non-transitory computer-readable medium including executable instructions, which when executed by circuitry, causes the circuitry to execute the method.

In one implementation, an apparatus for calibrating a photon-counting detector includes: means for receiving a reference signal, which is measured by a reference detector that measures an output from an X-ray tube, and means for determining, for a detector channel of the photon-counting detector, a mapping between a first true count rate on the detector channel without an object and the reference signal in accordance with a linear relationship between the reference signal and the first true count rate, based on a measured count rate on the detector channel and a predefined relationship between the first true count rate and the measured count rate.

A reference calibration is utilized to establish a mapping between a reference detector signal and a true count incident on a photon-counting detector. The true count rate/flux is then utilized to determine projection data from the detector, which is in turn utilized to generate images.

According to aspects of this disclosure, a reference calibration is executed to extract a mapping from a reference signal, which is relatively easy to measure, for true incident flux on a photon counting detector (PCD), which is relatively difficult or not possible to measure. A PCD can be used to measure incident flux even with the presence of pile-up and other effects resulting in count loss or inaccuracy. A filter can be used to reduce the flux and the effect is corrected using a known tube spectrum. Binned count data can be used to determine incident flux by using a detector response model that includes realistic pulse pile-up. A phantom can be used during calibration. With material decomposition, it is possible to determine the incident flux without the phantom.

Figure 1:
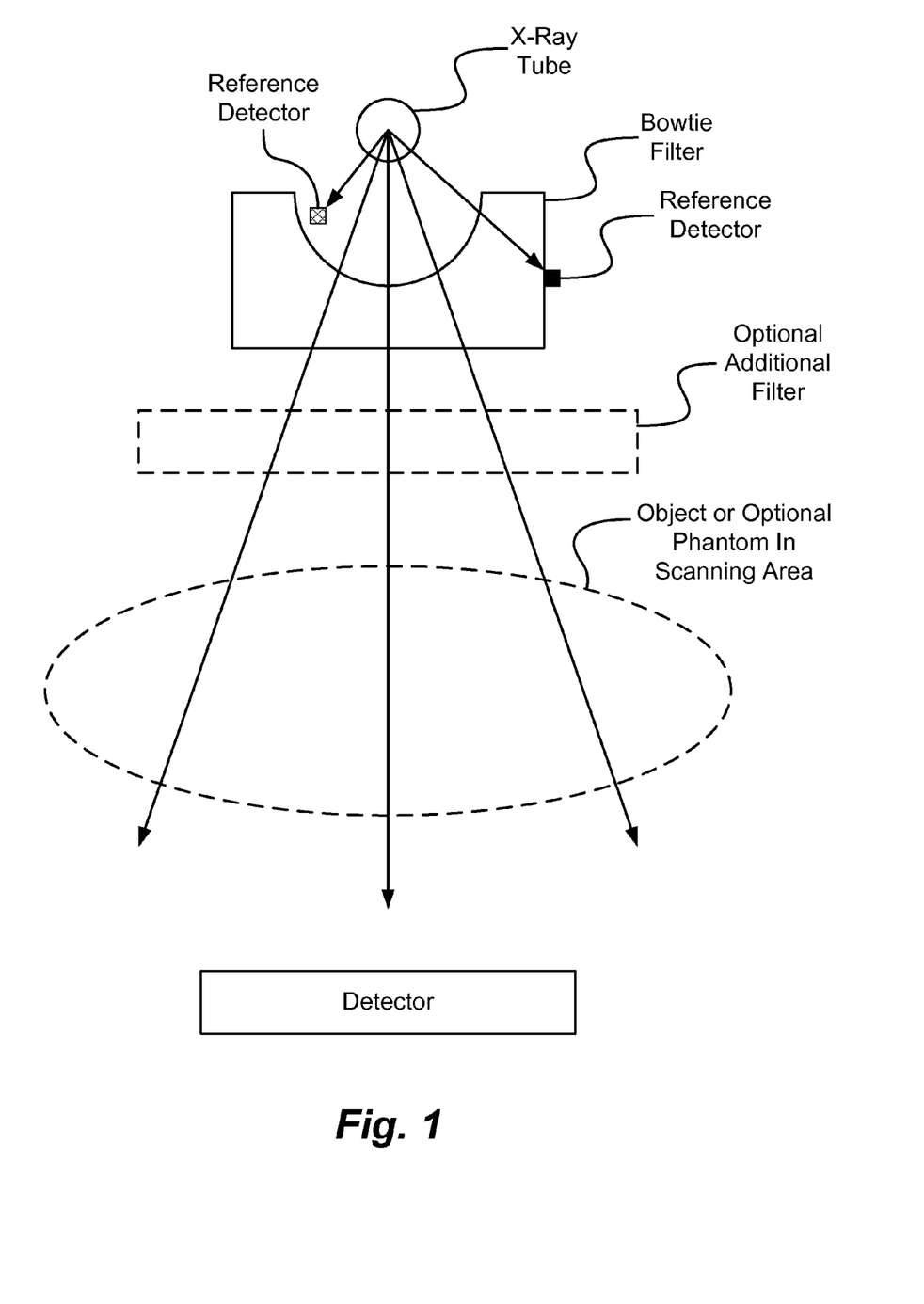
FIG. 1 is a schematic representation of a CT scanner including a reference detector.

FIG. 1 illustrates a CT scanner that utilizes a reference detector to monitor a variation of an X-ray tube during a scan in accordance with aspects of this disclosure. The CT scanner generally includes an X-ray tube, a bowtie filter, a reference detector, and a detector. A to-be scanned object is positioned in front of the detector, with respect to a radiating direction of the X-ray tube. As illustrated in FIG. 1, the reference detector can be located between the bowtie filter and the object in one implementation. The reference detector can also be located between the X-ray tube and the bowtie filter, as also illustrated in FIG. 1. In these and other implementations, the reference detector can be installed so as to rotate with the bowtie filter and the X-ray tube. Further, multiple reference detectors could be provided, and outputs thereof can be used to create an average reference signal that is used for reference calibration. Also, multiple reference calibrations can be obtained by using multiple reference detectors, where the reference calibrations can be averaged or statistically changed to obtain a summary reference calibration.

According to aspects of implementations of this disclosure, an additional filter can be additionally/optionally included. Further, a phantom can be additionally/optionally included, as illustrated in FIG. 1. Also, in one implementation, the bowtie filter can be removed or not utilized.

The CT scanner can use a non-spectral reference detector. The reference detector is an energy-integrating detector, and only measures X-ray intensity variations. The reference detector does not measure spectrum variation.

In spectral CT scanners using photon-counting detectors (PCDs), detected counts are generally fewer than the true counts due to pile-up problems at medium to high fluxes. Count loss and count nonlinearity occurs as incident flux increases. This is in contrary to conventional energy-integrating CT detectors, where an output is very linear to input intensity.

In FIG. 1, the dimensions and distances illustrated therein are not scalable to actual numbers. Also, the actual position of the reference detector with respect to the x-ray tube can vary from system to system. That is, different manufacturers and different generations of systems place the reference detector in different locations. However, the reference detector is at a fixed position with respect to the x-ray tube and bowtie filter, and these elements rotate together.

To determine PCD projection data, which is used to construct or generate images, the true count rate ($n_{PCD}$) incident on the PCDs is required. Pile-up correction is discussed in U.S. application Ser. No. 13/866,695, filed Apr. 19, 2013, which is incorporated herein by reference. Pile-up correction enables photon counting spectral CT and requires knowledge of the true count rate, $n_{PCD}$. The true count rate is the number of counts per unit time per unit detector channel. In the following descriptions, "count" and the variables associated with "n" refer to count rates, which is different from a total number of counts accumulated over a time period, which utilizes variables associated with "N." In accordance with the implementations discussed herein, a reference calibration provides a mapping between a reference signal (e.g., from a reference detector) and a count rate.

In other words, a reference calibration is utilized to establish a mapping between a reference detector signal and a true count rate on the PCD.

For a given incident spectrum, the following relationship exists: $n_{PCD}^{air} \propto I_{ref}$.

A signal from an energy-integrating reference detector is $I_{ref} = T \cdot n_{ref}^{air} \cdot \int dE \cdot E \cdot S_{ref}(E)$, where T is the integration time, $n_{ref}^{air}$ is the count rate at the reference detector, E is the energy factor, and $S_{ref}(E)$ is the normalized spectrum at the reference detector. From FIG. 1, given a same spectrum, $n_{PCD}^{air} \propto n_{ref}^{air}$ since they only differ by geometrical factors (i.e., different distances to the X-ray tube) and attenuation paths to the X-ray tube (different bowtie paths, filter paths, etc.). Therefore, $n_{PCD}^{air} \propto I_{ref}$.

A constant A is determined such that $n_{PCD}^{air} = A \cdot I_{ref}$, where $I_{ref}$ is the reference detector signal (arbitrary unit), and $n_{PCD}^{air}$ is the true count rate (i.e., the true count rate across all energies) on the PCD without an object. $n_{PCD}$ is then determined from $n_{PCD}^{air}$ and a basis material thickness $\{L_1, L_2\}$ in accordance with Equation (1), as follows.

$$n_{PCD} = n_{PCD}^{air} \cdot \int dE \cdot S^{air}(E) e^{-\mu_1(E)L_1 - \mu_2(E)L_2} \quad (1)$$

$S^{air}(E)$ is the normalized tube spectrum without the object after the bowtie, which is known to the manufacturer.

PCDs encounter pile-up and count loss at clinically relevant X-ray fluxes. The detected counts on PCDs are generally fewer than the true counts. An inaccurate $n_{PCD}^{air}$ measurement will result in an error in the constant A. Also, using a lower tube current can avoid pile-up and count loss. A problem with a lower tube current (mA) is that measurements will be very noisy and more subject to statistical error. Also, when the tube current (mA) is lower, the tube current (mA) may not be stable. However, it is not a problem itself when the tube current (mA) is not stable because this is linearly reflected in both $I_{ref}$ and $n_{PCD}$, and does not affect a reference mapping.

Signals from a standard energy-integrating reference detector can be utilized to derive a true number of photon counts for each photon-counting detector channel in a way that enables accurate modeling and compensation of pile-up and other non-ideal aspects of the detector response. Discussed below are four solutions based on a linear relationship between a reference signal and a counting flux at the photon counting detectors (PCDs).

Solution A

Solution A is directed to a non-linear mapping for a reference calibration, f. Here, $$n_{PCD}^{air} = A \cdot I_{ref}, \text{ and}$$

$$\hat{n}_{PCD}^{air} = f(n_{PCD}^{air}) = f(A \cdot I_{ref}) \quad (3)$$

$I_{ref}$ is the reference detector signal (an arbitrary unit), and $\hat{n}_{PCD}^{air}$ is the measured count rate on the PCD without an object.

The reference calibration f reflects a pile-up effect resulting in count loss and non-linearity. f can be any function found, either theoretically or empirically, to describe detector counting behavior. Examples include:
1. Paralyzable model: $\hat{n}_{PCD}^{air} = A \cdot I_{ref} e^{-\tau A I_{ref}}$, where A and τ are calibration parameters;
2. First non-paralyzable model:

$$\hat{n}_{PCD}^{air} = \frac{A \cdot I_{ref}}{1 + \tau A I_{ref}},$$

where A and τ are calibration parameters; and
3. Second non-paralyzable model:

$$\hat{n}_{PCD}^{air} = \frac{1}{\tau}(1 - e^{-\tau A I_{ref}}),$$

where A and τ are calibration parameters.

For the paralyzable model and the first non-paralyzable model, A and τ can be derived from classic Poisson statistics. See "Radiation detection and measurement," by Glenn Knoll, 2010, which is incorporated herein by reference.

For the second non-paralyzable model, A and τ can be derived in view of C. Szeles et al., "CdZnTe Semiconductor Detectors for Spectroscopic X-ray Imaging," IEEE Transactions on Nuclear Science, vol. 55, p. 572, February 2008, which is incorporated herein by reference.

Parameter A is dependent on incident spectrum: kVp, source filtration, bowtie filter, etc. Parameter A is also dependent on polar angle (if applied in a sparse 4$^{th}$-generation geometry CT scanner).

A, which does not depend on detector properties, is determined from the selected model and τ, which incorporates the known detector properties. τ can be measured and is a characteristic of the detector. τ does not depend on incident spectra or polar angle, and is a parameter that describes the linearity of a measured count rate of the detector. τ can be known a priori or estimated. A varies for every spectrum, and changes with polar angle for 4th generation geometries. For a fixed spectrum, A will remain the same.

Incident flux from the X-ray tube is not reduced (e.g., by an optional filter or otherwise) in determining the non-linear mapping for the reference calibration, f, according to one implementation of Solution A.

Solution B

Solution B is directed to utilizing an additional filter (i.e., the optional additional filter in FIG. 1 without an object or a phantom in one implementation) to reduce the flux in an air scan. This filter does not affect the flux to the reference detector illustrated in FIG. 1. Here, the true count rate in the air scan with the additional filter is characterized as:

$$n_{PCD}^{air} = A \cdot I_{ref}$$

The true count rate in the air scan with the additional filter is characterized as:

$$n'_{PCD}{}^{air} = A' \cdot I_{ref}, \text{ where } n'_{PCD}{}^{air} \text{ and } I_{ref} \text{ are measured.}$$

The true count rates with and without the additional filter are related to each other by the following relationship:

$$n'_{PCD}{}^{air} = n_{PCD}{}^{air} \int dE S^{air}(E) e^{-\mu_F(E) l_F}.$$

Here, $\mu_F(E)$ is the linear attenuation coefficient of the additional filter, $l_F$ is the path length in the additional filter, and $S^{air}$ indicates the spectrum in air. Parameter A is related to A' by the following relationship:

$$A' = A \int dE S^{air}(E) e^{-\mu_F(E) l_F}. \quad (4)$$

In (4), A is found because A' is known from the ratio of the air count rate with filtration to the reference signal.

Solution C

Solution C is directed to utilizing different energy bins to find A. Here, let E represent a particular energy bin and its energy range. To simplify notation, let $n = n_{PCD}{}^{air}$. Then, N(E) is the measurement of counts of the PCD in bin E:

$$N(E) = T_{PCD} \{n e^{-n\tau} \int dE_0 R_1(E,E_0) S(E_0) + n^2 e^{-n\tau} \iint dE_0 dE_1 R_2(E,E_0,E_1) S(E_0) S(E_1)\}.$$

Here, N is a count, while the count rate is n, and $T_{PCD}$ is an integrating time.

The spectrum, S, is assumed known. The detector response functions, $R_1$ and $R_2$, are also assumed known. n, which is a count rate across all energies, can be solved for various mA (tube currents) to determine the relationship to $I_{ref}$. Once n is obtained, the relationship with $I_{ref}$ can be utilized to find A, $n_{PCD}{}^{air} = A \cdot I_{ref}$.

$R_1$ and $R_2$ (detector response models, functions, matrices, etc.) can be obtained in a manner consistent with the teachings of U.S. application Ser. No. 13/866,695, filed Apr. 19, 2013, which is incorporated herein by reference.

$E_0$ and $E_1$ are energy levels, and represent true energy(s) of the incident x-ray event(s). E is the detected energy of an x-ray event, as reported by a detector. E is different from $E_0$ and $E_1$ due to realistic detector responses, $R_1$ and $R_2$ (the purpose of $R_1$ and $R_2$ is to quantitatively characterize the realistic, non-perfect behavior of a detector). In other words, $R_1(E,E_0)$ is the probability of an incident x-ray event with energy $E_0$ being detected as E, and $R_2(E,E_0,E_1)$ is the probability of two incident x-ray events (with energies $E_0$ and $E_1$, respectively) being detected as E.

In Solution C, counts are used for each energy bin. While in Solution A, a total flux across all energy is utilized.

Solution D

Solution D is directed to utilizing a phantom (i.e., the optional phantom illustrated in FIG. 1, without an object or an optional additional filter in one implementation) for calibration instead of an air scan. $3^{rd}$-generation CT scanner data is utilized at two different kVps (peak kilovoltages) to perform material decomposition. A basis thickness, $L_1$ and $L_2$, is calculated or given/provided/obtained through manufacturer specifications. The basis thickness $L_1$ and $L_2$ can also be estimated, If needed, the basis thickness is reconstructed in a $3^{rd}$-generation geometry and re-projected to a $4^{th}$-generation geometry.

One of the previous proposed solutions, such as linear or non-linear mapping according to Solution A, is utilized to determine n' with the phantom present. Then, $n_{PCD}{}^{air}$ is determined according to:

$$n' = n_{PCD}{}^{air} \int dE_0 S(E_0) e^{-\mu_1(E_0) L_1 - \mu_2(E_0) L_2}, \text{ where } n' \text{ is measured.}$$

The spectrum S is the known spectrum without the object (i.e., without the phantom present). Once $n_{PCD}{}^{air}$ is obtained, the relationship with $I_{ref}$ can be utilized to find A, $n_{PCD}{}^{air} = A \cdot I_{ref}$.

In some aspects, this solution (Solution D) is similar to Solution B in that flux is reduced. On the other hand, flux is not reduced in Solutions A and C.

Exemplary Implementations of Processes

Reference calibration is utilized to extract mapping from a reference signal, which is relatively easy to measure, for true incident flux on a PCD, which is relatively difficult or impossible to measure. PCDs can be utilized to measure incident flux even with the presence of pile-up and other effects resulting in count loss or inaccuracy. A filter can be utilized to reduce the flux and the effect is corrected using a known tube spectrum. Binned count data can also be used to determine incident flux by using a detector response model that includes a realistic pulse pile-up. A phantom can be utilized during calibration. However, with material decomposition, it is possible to determine the incident flux without the phantom.

Full Scan Data Correction

Full scan data correction is a complex process, and will incorporate the calibration outcomes described herein, together with other components and algorithms according to conventional techniques. Aspects of this disclosure are directed to a portion of a full scan data correction process a calibration algorithm and a data correction algorithm based on a calibration of the calibration algorithm.

$E_0$ and $E_1$ represent true energy(s) of the incident x-ray event(s). E is the detected energy of the x-ray, reported by a detector. E is different from $E_0$ and $E_1$ due to realistic detector response, $R_1$ and $R_2$ (the purpose of $R_1$ and $R_2$ is to quantitatively characterize this realistic, non-perfect behavior of a detector). In other words, $R_1(E, E_0)$ is the probability of an incident x-ray event with energy $E_0$ being detected as E; R2(E, $E_0$, $E_1$) is the probability of two incident x-ray events (energy $E_0$ and $E_1$, respectively) being detected as E.

$3^{rd}$-Generation PCD Spectral CT Geometry (No Polar Effect)

Calibration

For every PCD channel, A is determined (to subsequently determine $n_{PCD}{}^{air}$) using one of the Solutions A-D. This is done for every kVp and bowtie combination. A combination includes a particular kVp and a particular bowtie geometry or shape. Two or more kVp levels can be utilized and/or a plurality of bowtie geometry or shapes can be utilized result in a plurality of combinations. An exemplary algorithm for such a calibration is discussed in the following with reference to FIG. 2.

Figure 2:
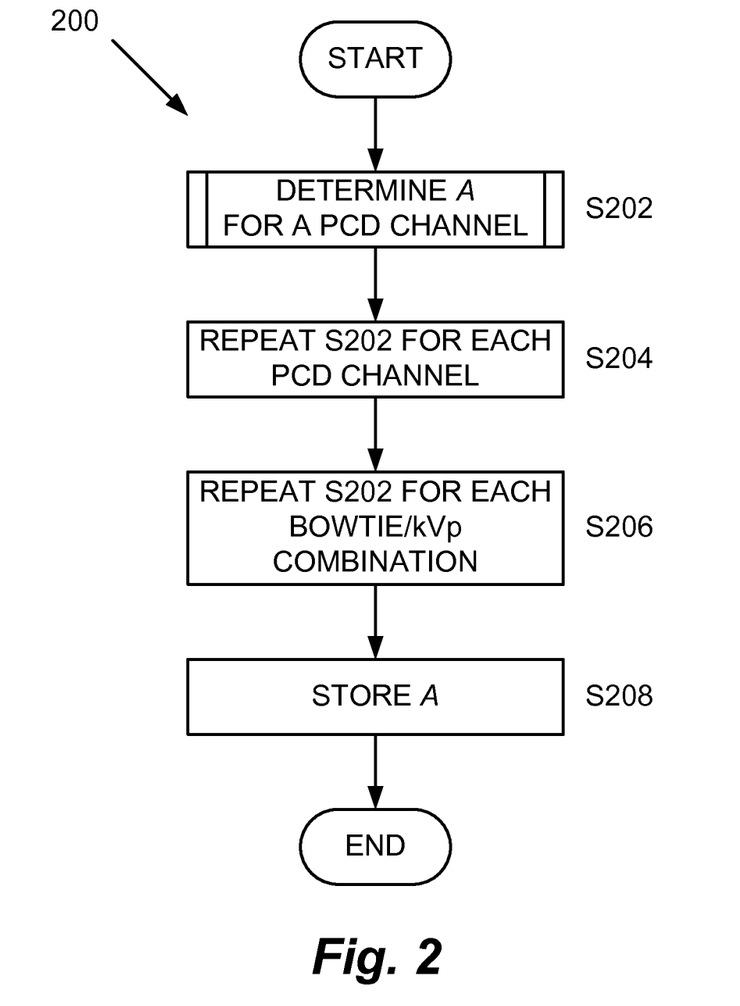
FIGS. 2-5 illustrate algorithmic processes, by way of flowcharts, for reference calibration and scan data correction for $3^{rd}$ and $4^{th}$ generation PCD spectral CT geometries.

FIG. 2 illustrates exemplary algorithm 200, which is a calibration algorithm for a $3^{rd}$-generation PCD spectral CT geometry. At S202, A is determined for a PCD channel. This determination is in accordance with one of the solutions (i.e., one of Solutions A-D) discussed herein. At S204, S202 is repeated for each PCD channel. Thus, A is determined for every PCD channel in accordance with one of Solutions A-D. This is executed at a single combination of kVp and bowtie. At S206, S202-S204 are repeated for every combination of kVp and bowtie, and at S208 the resulting values of A for the various combinations of PCD channel and kVp and bowtie are stored.

Scan Data Correction

For every PCD channel, $n_{PCD}{}^{air}$ is calculated based on A and $I_{ref}$, and $n_{PCD}$ is calculated in accordance with (1), utilizing $n_{PCD}{}^{air}$ and known or current/best estimates of $\{L_1, L_2\}$. $n_{PCD}$ is then applied to raw data pile-up correction, and corrected projection data is calculated. This is done for every view. An exemplary algorithm for such a correction is discussed in the following with reference to FIG. 3.

Figure 3:
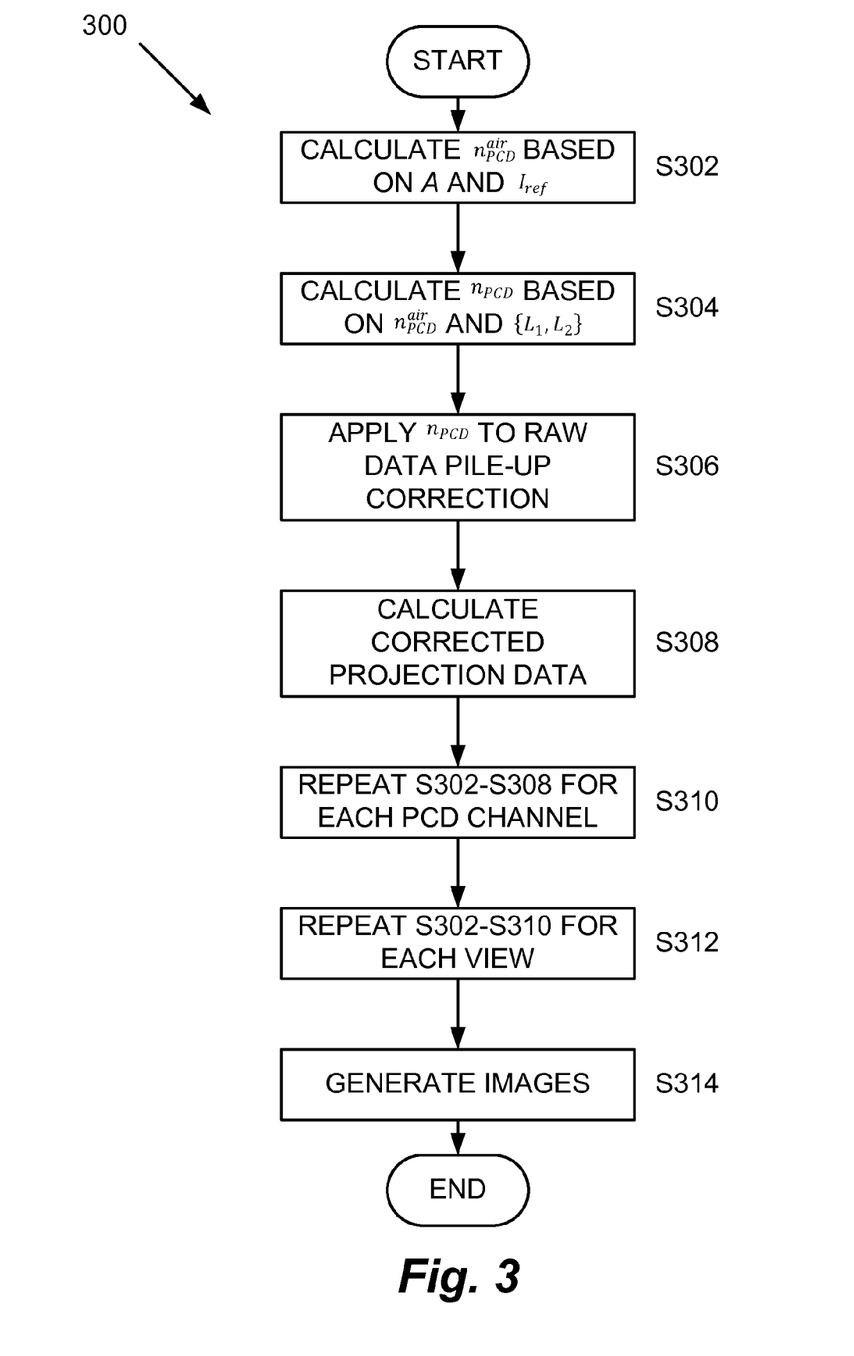

FIG. 3 illustrates exemplary algorithm 300, which is a scan data correction algorithm for a $3^{rd}$-generation PCD spectral CT geometry. At S302, $n_{PCD}^{air}$ is calculated based on A (stored at S208 in algorithm 200) and $I_{ref}$ and $n_{PCD}$ for a PCD channel is calculated at S304 according to (1) using the calculated $n_{PCD}^{air}$ and known or current/best estimates of $\{L_1, L_2\}$. The resulting values for $n_{PCD}$ are applied to raw data pile-up correction at S306, and corrected projection data is calculated based thereon at S308. At S310, S302-S308 are repeated for each PCD channel, and at S312, S302-S310 are repeated for each view. Images can then be generated from the resulting projection data at S314.

Sparse $4^{th}$-Generation PCD Spectral CT Geometry (Including Polar Effect)

Calibration

For every polar angle, A is determined (to subsequently determine $n_{PCD}^{air}$) using one of the Solutions A-D. This is done for every PCD channel. Further, this is done for every kVp and bowtie combination. An exemplary algorithm for such a calibration is discussed in the following with reference to FIG. 4.

Figure 4:
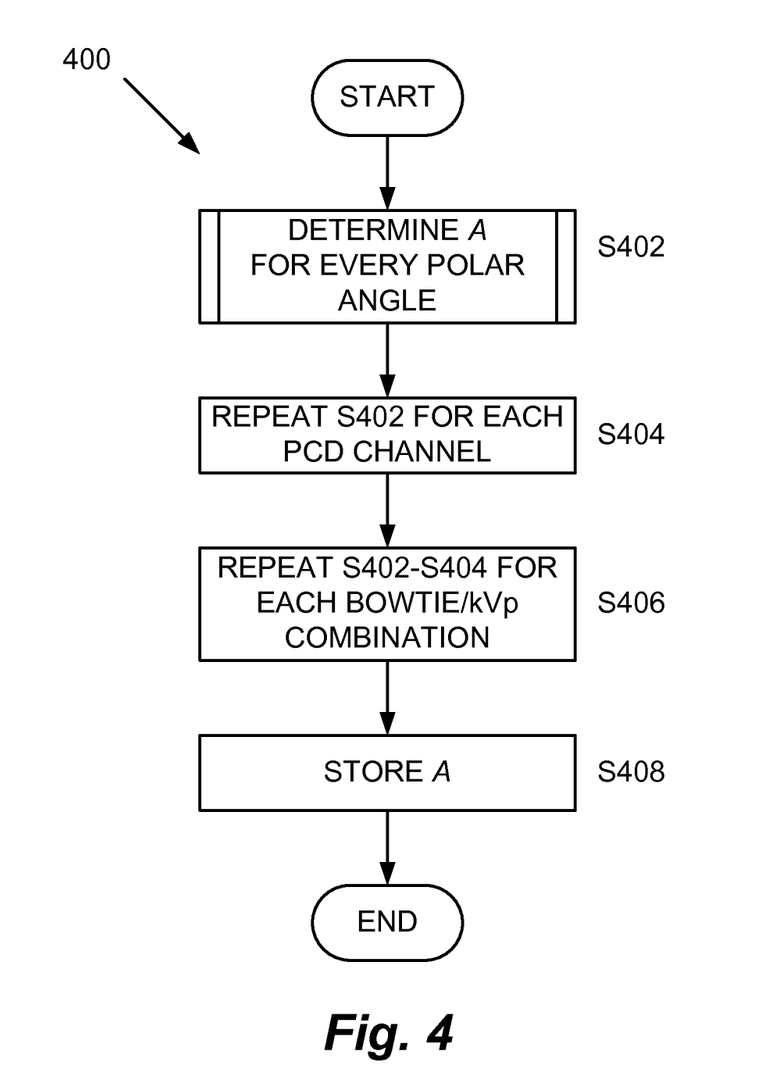

FIG. 4 illustrates exemplary algorithm 400, which is a calibration algorithm for a $4^{th}$-generation PCD spectral CT geometry. At S402, A is determined for every polar angle (i.e., for each polar angle) for a particular PCD channel and for a particular combination of kVp and bowtie. This determination is in accordance with one of the solutions (i.e., one of Solutions A-D) discussed herein. At S404, S402 is repeated for each PCD channel. Thus, A is determined for every polar angle for every PCD channel in accordance with one of Solutions A-D. At S406, S402-S404 are repeated for every combination of kVp and bowtie, and at S408 the resulting values of A for the various combinations of polar angle, PCD channel, and kVp and bowtie are stored.

Scan Data Correction

For every polar angle (which can be considered as equivalent to every view in a $3^{rd}$-generation geometry), $n_{PCD}^{air}$ is calculated based on A and $I_{ref}$ and $n_{PCD}$ is calculated in accordance with (1), utilizing $n_{PCD}^{air}$ and known or current/best estimates of $\{L_1, L_2\}$. $n_{PCD}$ is then applied to raw data pile-up correction, and corrected projection data is calculated. This is done for every PCD channel. An exemplary algorithm for such a correction is discussed in the following with reference to FIG. 5.

Figure 5:
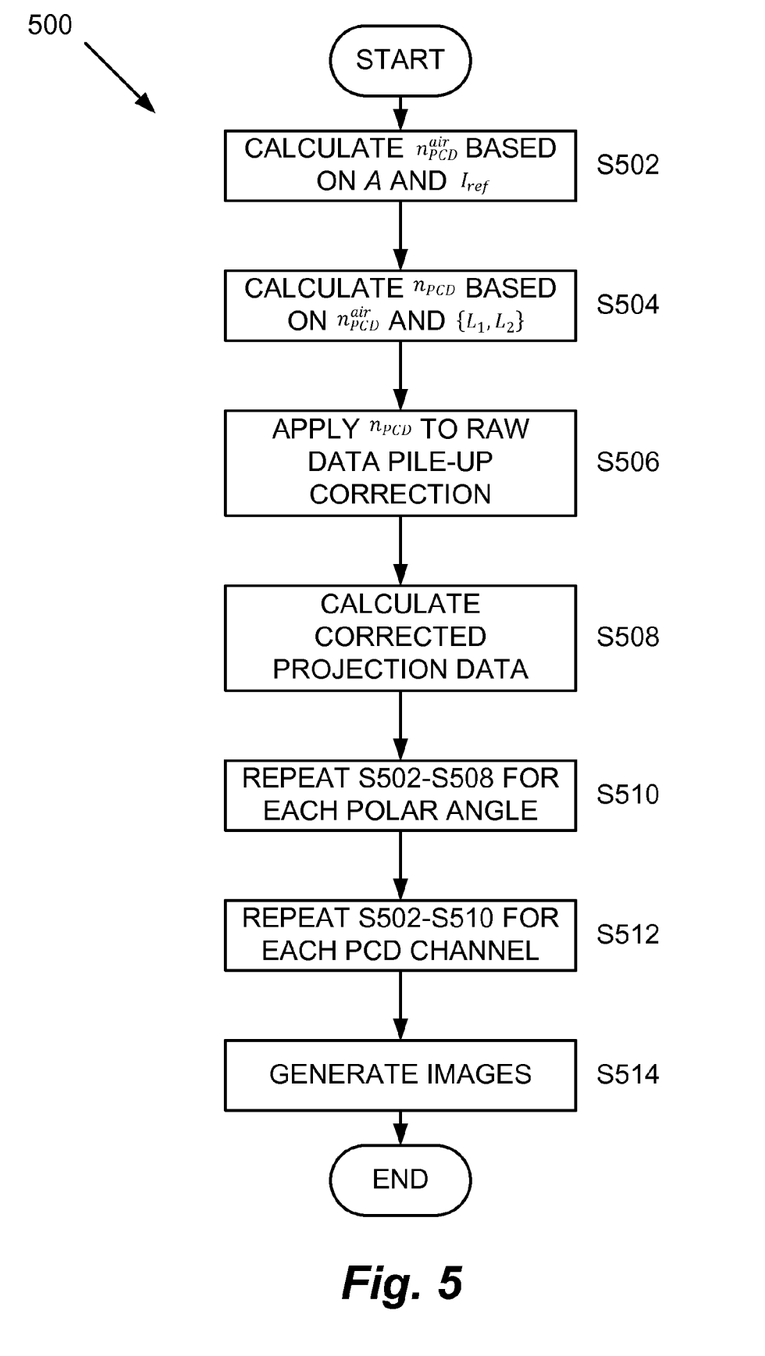

FIG. 5 illustrates exemplary algorithm 500, which is a scan data correction algorithm for a $4^{th}$-generation PCD spectral CT geometry. At S502, $n_{PCD}^{air}$ is calculated based on A (stored at S408 in algorithm 400) and $I_{ref}$ and $n_{PCD}$ for a particular PCD channel and polar angle is calculated at S504 according to (1) using the calculated $n_{PCD}^{air}$ and known or current/best estimates of $\{L_1, L_2\}$. The resulting values for $n_{PCD}$ are applied to raw data pile-up correction at S506, and corrected projection data is calculated based thereon at S508. At S510, S502-S508 are repeated for each polar angle of the particular PCD channel, and at S512, S502-S510 are repeated for each PCD channel. Images can then be generated from the resulting projection data at S514.

Exemplary Implementations of Systems

Figure 6:
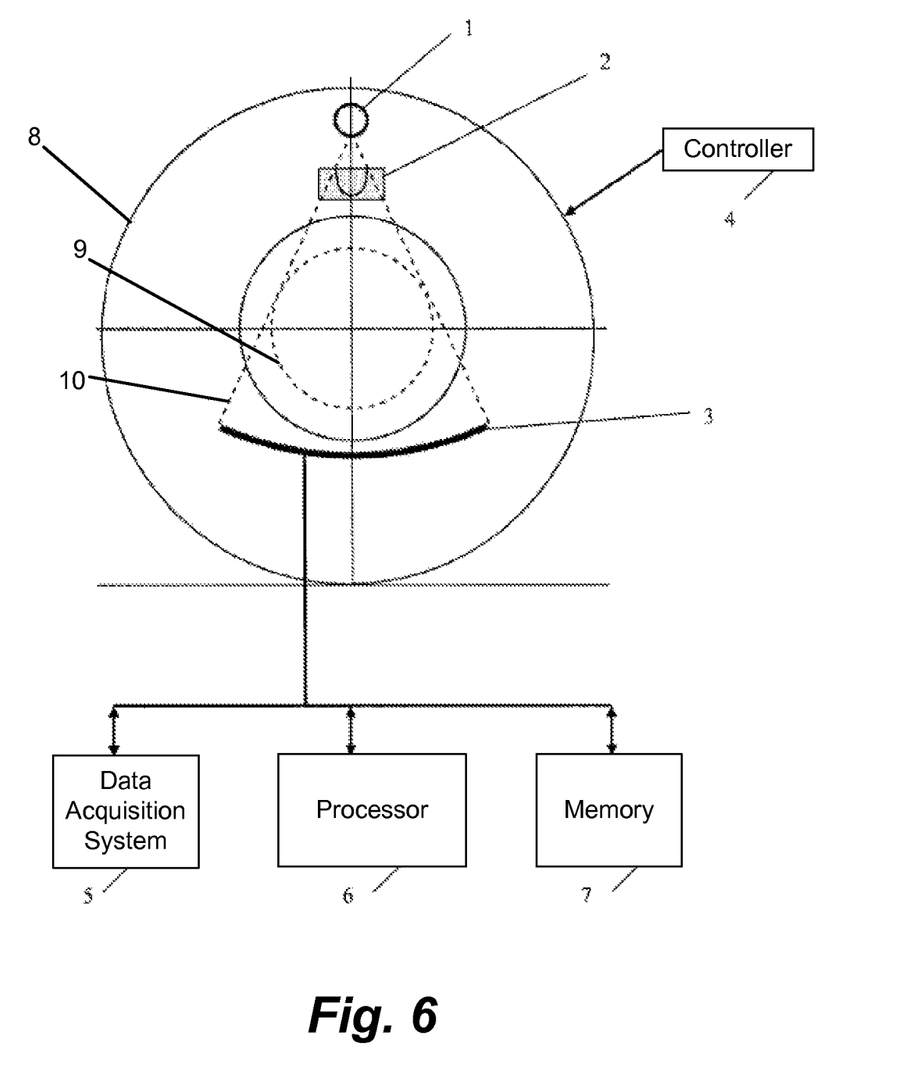
FIGS. 6 and 7 illustrate exemplary CT scanner systems.

FIG. 6 illustrates a simplified schematic structure of a CT apparatus that can include a detector array to detect photons. Aspects of this disclosure are not restricted to a CT apparatus as the medical imaging system. In particular, the structures and procedures described herein can be applied to other medical imaging systems, and the descriptions provided herein specifically relating to a CT apparatus and the detection of photons should be considered as exemplary.

Figure 7:
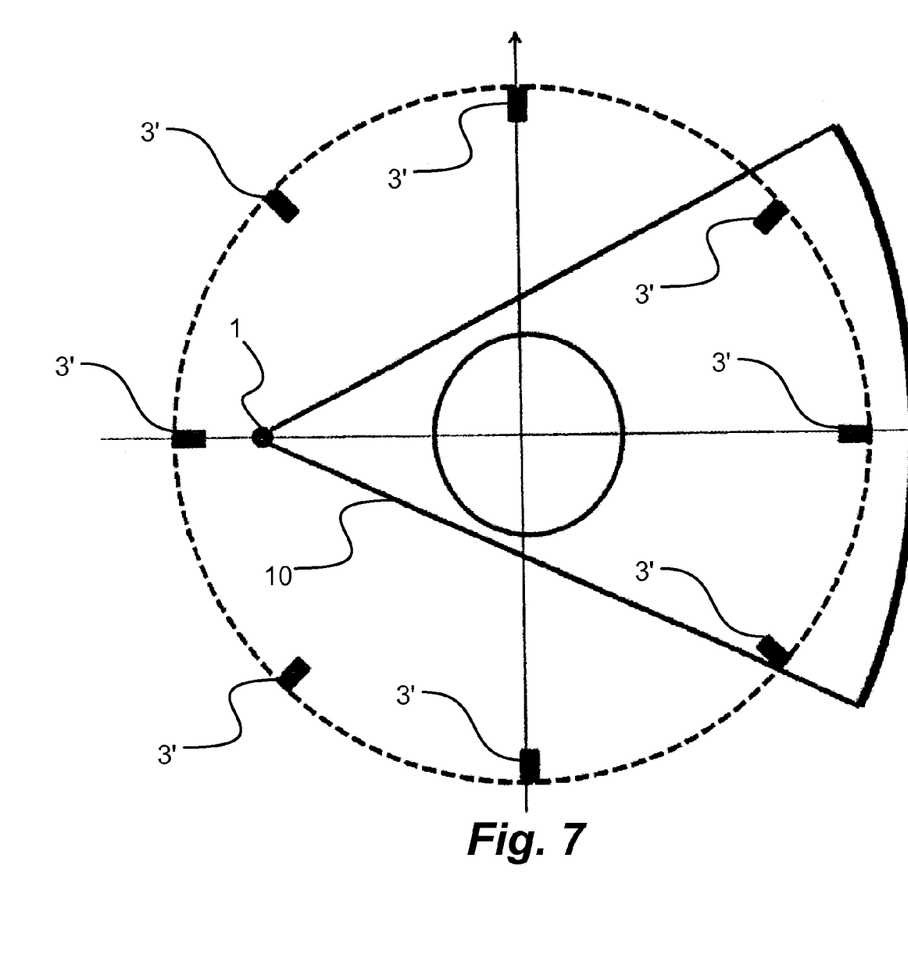

A detector array, a photon detector and/or a photon detector array may be referred to herein merely as a detector. The CT apparatus illustrated in FIG. 6 includes an X-ray tube 1, filters and collimators 2, and a detector 3. The CT apparatus can also include sparse fixed energy-discriminating (e.g., photon-counting) detectors 3', which can be arranged at a different radius from that of the third-generation detector, as shown in FIG. 7. The CT apparatus also includes additional mechanical and electrical components such as a gantry motor and a controller 4 to control the rotation of the gantry, control the X-ray source, and control a patient bed. The CT apparatus also includes a data acquisition system 5 and a processor 6. The processor 6 is configured to generate CT images based on the projection (view) data acquired by the data acquisition system. For example, the processor 6 includes a reconstruction processor to reconstruct spectral CT images. The processor is programmed to perform methods and execute algorithms in accordance with the processes, algorithms, equations and relationships described herein. The processor and data acquisition system can make use of a memory 7, which is configured to store, e.g., data obtained from the detector, detector pile-up models, and reconstructed images.

The X-ray tube 1, filters and collimators 2, detector 3, and controller 4 can be provided in a frame 8 that includes a bore. The frame 8 has a general cylindrical or donut shape. In the view shown in FIG. 6, a longitudinal axis of the bore of the frame 8 is in the center of the bore and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis. The processor 6 is programmed to determine photon counts of captured incident X-ray photons. The data acquisition system 5, the processor 6, and the memory 7 can be implemented as a single machine or computer, or as separate machines or computers that are coupled together or distributed via a network or other data communication system. The controller 4 can also be coupled via the network or other data communication system, and can be implemented by a separate machine or computer, or as part of another machine or computer of the system.

In FIG. 6, the detector 3 is a rotational detector array that rotates with the X-ray tube 1 with respect to the longitudinal axis. Although not shown in FIG. 6, a stationary detector array can also be included, thus providing a rotating detector array and a stationary array, together, in the frame 8. Other detectors can be implemented.

Figure 8:
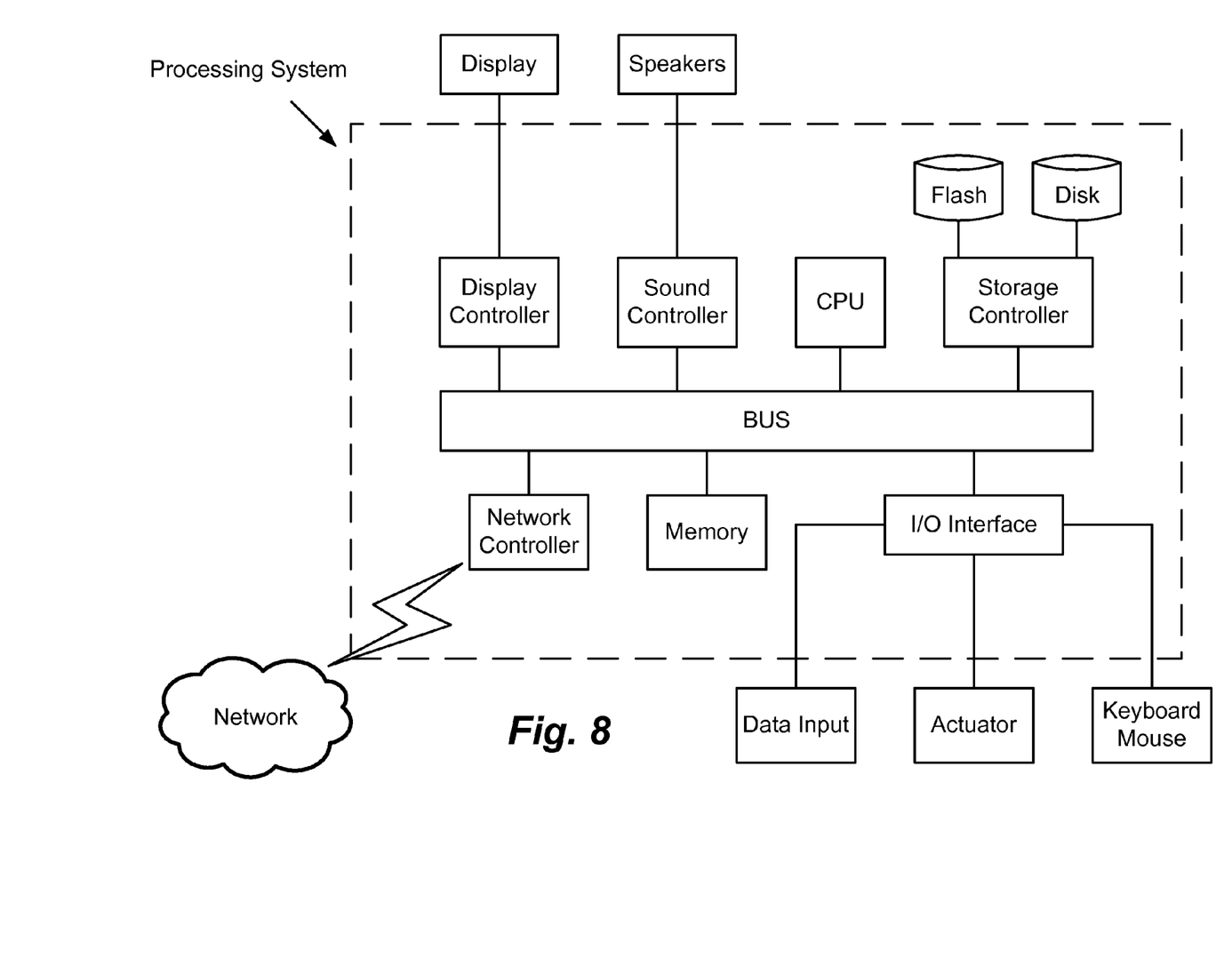
FIG. 8 is a schematic diagram of an exemplary processing system.

With reference to the structures illustrated in FIG. 6, an exemplary processing system is illustrated in FIG. 8, which is an exemplary implementation of the processor 6 of FIG. 6. This exemplary processing system can be implemented using one or more microprocessors or the equivalent, such as a central processing unit (CPU) and/or at least one application specific processor ASP (not shown). The microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central BUS is provided to connect the above hardware components together and provides at least one path for digital communication there between.

The data acquisition system 5, the processor 6, and the memory 7 of FIG. 6 can be implemented utilizing one or more processing systems in accordance with the exemplary implementation shown in FIG. 8. In particular, circuitry, one or more circuits or computer hardware units coinciding with one or more of the devices illustrated in FIG. 8 can provide for the functions of the data acquisition system 5, the processor 6, and the memory 7 (collectively or separately). The functional processing described herein can also be implemented in specialized circuitry or one or more specialized circuits including circuits to perform the described processing. Such circuits can be a part of a computer processing system or a discrete device that is interconnected to other systems. A processor in accordance with this disclosure can also be programmed to or configured to execute the functional processing described herein by computer code elements.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The Data Input portion of the processing system accepts input signals from a detector or an array of detectors by, e.g., respective wired connections. A plurality of ASICs or other data processing components can be provided as forming the Data Input portion, or as providing input(s) to the Data Input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. An apparatus for calibrating a photon-counting detector, comprising:
 circuitry configured to:
  receive a reference signal, which is measured by a reference detector that measures an output from an X-ray tube, and
  determine, for a detector channel of the photon-counting detector, a mapping between a first true count rate on the detector channel without an object and the reference signal, based on a measured count rate on the detector channel and a predefined relationship between the first true count rate and the measured count rate.

2. The apparatus according to claim 1, wherein the circuitry is further configured to:
 determine the mapping for each of a plurality of detector channels of a plurality of photon-counting detectors, and for each of a plurality of combinations of a bowtie filter and peak kilovoltage of the X-ray tube, and
 store a plurality of corresponding values for the mapping.

3. The apparatus according to claim 2, wherein the circuitry is further configured to:

calculate second true count rates on the detector channel based on the stored values for the mapping and reference signals from the reference detector during a scan of the object;

calculate third true count rates on the detector channel with the object based on the calculated second true count rates and a basis material thickness of the object; and apply the third true count rates to raw data pile-up correction and calculate projection data based thereon for each of the detector channels and for each of a plurality of views of the object.

4. The apparatus according to claim 3, wherein the circuitry is further configured to generate images from the projection data.

5. The apparatus according to claim 2, wherein the circuitry is further configured to determine the mapping for each of a plurality of polar angles.

6. The apparatus according to claim 5, wherein the circuitry is further configured to:

calculate second true count rates on the detector channel based on the stored values for the mapping and reference signals from the reference detector during a scan of the object;

calculate third true count rates on the detector channel with the object based on the calculated second true count rates and a basis material thickness of the object; and apply the third true count rates to raw data pile-up correction and calculate projection data based thereon for each of the plurality of polar angles and for each of the detector channels.

7. The apparatus according to claim 6, wherein the circuitry is further configured to generate images from the projection data.

8. The apparatus according to claim 1, wherein:

the predefined relationship between the first true count rate, $n_{PCD}^{air}$, and the measured count rate is $\hat{n}_{PCD}^{air} = f(n_{PCD}^{air}) = f(A \cdot I_{ref})$, where $\hat{n}_{PCD}^{air}$ is the measured count rate, f is a reference calibration function that reflects a pile-up effect resulting in count loss and non-linearity, $I_{ref}$ is the reference signal, and A is the mapping and is a derived parameter that does not depend on properties of the photon-counting detector.

9. The apparatus according to claim 8, wherein:

$f(A \cdot I_{ref})$ is equal to one of:

$$A \cdot I_{ref} e^{-\tau A I_{ref}},$$

$$\frac{A \cdot I_{ref}}{1 + \tau A I_{ref}}, \text{ and}$$

$$\frac{1}{\tau}(1 - e^{-\tau A I_{ref}}),$$

where $\tau$ is a calibration parameter that describes a linearity of a measured count rate of the photon-counting detector.

10. The apparatus according to claim 1, wherein the predefined relationship between the first true count rate, $n_{PCD}^{air}$, and the measured count rate is:

$n_{PCD}^{air} = A \cdot I_{ref}$, and $n'_{PCD}^{air} = A' \cdot I_{ref} = n_{PCD}^{air} \int dE S^{air}(E) e^{-\mu_F(E) l_F}$, where $I_{ref}$ is the reference signal, $\mu_F(E)$ is a linear attenuation coefficient of an additional filter that is provided between the X-ray tube and the photon counting detector, $n'_{PCD}^{air}$ is the measured count rate with the additional filter, $l_F$ is a path length in the additional filter, $S^{air}$ indicates a spectrum in air, A is the mapping, A' is the mapping with the additional filter, and $A' = A \int dE S^{air}(E) e^{-\mu_F(E) l_F}.$ 11. The apparatus according to claim 1, wherein the predefined relationship between the first true count rate, $n_{PCD}^{air}$, and the measured count rate is:

$n_{PCD}^{air} = A \cdot I_{ref}$ and $N(E) = T_{PCD}\{ne^{-n\tau} \int dE_0 R_1(E, E_0) S(E_0) + n^2 e^{-n\tau} \int\int dE_0 dE_1 R_2(E, E_0, E_1) S(E_0) S(E_1)\}$, where $n = n_{PCD}^{air}$, N(E) is a measured number of counts from the photo counting detector in an energy bin E that has a particular energy range, S is a spectrum, $R_1$ and $R_2$ are detector response functions, $I_{ref}$ is the reference signal, A is the mapping, n is solved for various currents to determine a relationship to $I_{ref}$, and after n is obtained, the relationship between n and $I_{ref}$ is utilized to find A, according to $n_{PCD}^{air} = A \cdot I_{ref}$.

12. The apparatus according to claim 1, wherein the predefined relationship between the first true count rate, $n_{PCD}^{air}$, and the measured count is:

$n_{PCD}^{air} = A \cdot I_{ref}$ and $n' = n_{PCD}^{air} \int dE_0 S(E_0) e^{-\mu_1(E_0) L_1 - \mu_2(E_0) L_1}$, where n' is the measured count rate, $L_1$ and $L_2$ represent a basis thickness of a phantom provided between the X-ray tube and the photon counting detector and $\mu_1$ and $\mu_2$ are corresponding linear attenuation coefficients of the phantom, $I_{ref}$ is the reference signal, A is the mapping, and $E_0$ is a true energy of an incident X-ray from the X-ray tube and two or more values for the true energy are utilized.

13. The apparatus according to claim 1, further comprising:

the X-ray tube;

a bowtie filter provided between the X-ray tube and a scanning area for scanning an object;

the reference detector provided such that a portion of the X-rays output from the X-ray tube are detected by the reference detector; and photon detectors to measure X-ray intensity and a spectrum of X-rays from the X-ray tube that pass through the scanning area.

14. The apparatus according to claim 13, wherein the reference detector is provided on or proximate to the bowtie filter on a side of the bowtie filter that is opposite to the X-ray tube such that a portion of the X-rays output from the X-ray tube pass through the bowtie filter and are detected by the reference detector.

15. The apparatus according to claim 13, wherein the reference detector is provided on or proximate to the bowtie filter, between the bowtie filter and the X-ray tube, such that a portion of the X-rays output from the X-ray tube are detected by the reference detector without passing through the bowtie filter.

16. The apparatus according to claim 1, wherein the reference detector is an energy-integrating detector, only measures X-ray intensity variations, and does not measure spectrum variation.

17. A method for calibrating a photon-counting detector, comprising:
receiving, by receiving circuitry, a reference signal, which is measured by a reference detector that measures an output from an X-ray tube, and
determining, by determining circuitry, for a detector channel of the photon-counting detector, a mapping between a first true count rate on the detector channel without an object and the reference signal, based on a measured count rate on the detector channel and a predefined relationship between the first true count rate and the measured count rate.

18. A non-transitory computer-readable medium including executable instructions, which when executed by circuitry, causes the circuitry to execute the method according to claim 17.

19. An apparatus for calibrating a photon-counting detector, comprising:
means for receiving a reference signal, which is measured by a reference detector that measures an output from an X-ray tube, and
means for determining, for a detector channel of the photon-counting detector, a mapping between a first true count rate on the detector channel without an object and the reference signal, based on a measured count rate on the detector channel and a predefined relationship between the first true count rate and the measured count rate.

20. An X-ray computed tomography apparatus, comprising:
an X-ray tube configured to generate X-rays;
a plurality of reference detectors configured to measure X-ray intensity generated by the X-ray tube as a reference signal;
a plurality of photon-counting detectors configured to measure a number of photon counts, which correspond to the X-rays generated by the X-ray tube, the photon-counting detectors being located at different positions from the plurality of reference detectors; and
calculation circuitry configured to determine, for a detector channel of the photon-counting detectors, a mapping between a true count on the detection channel without an object and the reference signal, based on the measured number of photon counts on the detector channel and a predetermined relationship between the true count rate and the measured number of photon counts, and to correct the measured number of photon counts on the detector channel using the determined mapping.

* * * * *